(12) United States Patent  (10) Patent No.: US 7,132,144 B2
Roberts  (45) Date of Patent: Nov. 7, 2006

(54) FASTENER TAPES

(75) Inventor: Jennifer Lynn Roberts, Windham, NH (US)

(73) Assignee: Velcro Industries B.V., Curacao (NL)

( * ) Notice: Subject to any disclaimer, the term of this patent is extended or adjusted under 35 U.S.C. 154(b) by 0 days.

(21) Appl. No.: 10/376,495

(22) Filed: Feb. 28, 2003

(65) Prior Publication Data

US 2004/0170792 A1  Sep. 2, 2004

(51) Int. Cl.
B32B 9/00 (2006.01)
(52) U.S. Cl. .......................... 428/40.2; 24/306; 24/452; 428/40.1; 428/41.3; 428/41.5; 428/41.9; 428/99; 428/100; 428/119; 428/120; 428/200; 428/346; 428/347; 428/350
(58) Field of Classification Search .............. 428/40.1, 428/119, 120, 99, 100, 200, 40.2, 413, 41.5, 428/41.9, 346, 347, 350; 24/306, 452
See application file for complete search history.

(56) References Cited

U.S. PATENT DOCUMENTS

| 3,353,663 A | 11/1967 | Kayser et al. |
| 3,752,619 A | 8/1973 | Menzin |
| 3,766,566 A | 10/1973 | Tadokoro |
| 3,925,858 A | 12/1975 | Thaeler |
| 4,012,350 A | 3/1977 | Burke, Jr. et al. |
| 4,035,961 A | 7/1977 | Pemrick et al. |
| 4,058,853 A | 11/1977 | Boxer et al. |
| 4,086,384 A | 4/1978 | Adelman et al. |
| 4,104,428 A | 8/1978 | Liu et al. |
| 4,165,555 A | 8/1979 | Boxer et al. |
| 4,263,360 A | 4/1981 | Adelman |
| 4,379,201 A | 4/1983 | Heilmann et al. |
| 4,794,028 A | 12/1988 | Fischer |
| 4,842,916 A | 6/1989 | Ogawa et al. |
| 4,850,085 A | 7/1989 | Murasaki |
| 4,855,170 A | 8/1989 | Darvell et al. |
| 4,894,060 A | 1/1990 | Nestegard |
| 5,006,393 A | 4/1991 | Isoe |
| 5,085,655 A | 2/1992 | Mann et al. |
| 5,321,855 A | 6/1994 | Ciuffo |
| 5,378,536 A | 1/1995 | Miller et al. |
| 5,389,438 A | 2/1995 | Miller et al. |
| 5,439,982 A | 8/1995 | Taylor et al. |
| 5,468,237 A | 11/1995 | Miller et al. |
| 5,486,256 A | 1/1996 | Romesberg et al. |
| 5,679,302 A | 10/1997 | Miller et al. |
| 5,699,557 A | 12/1997 | Johnson |

(Continued)

FOREIGN PATENT DOCUMENTS

EP  0 908 477 A1  4/1999

(Continued)

OTHER PUBLICATIONS www.velcro.com/industrial/pressure.html, Jun. 5, 2003.

(Continued)

Primary Examiner—Nasser Ahmad
(74) Attorney, Agent, or Firm—Fish & Richardson, P.C.

(57) ABSTRACT

Cooperative touch fasteners have a sheet-form base with an upper face and a lower face. Extending outwardly from, and integral with the upper face of the base is a plurality of fastener elements. Additionally, the lower face of the sheet-form base has a pressure adhesive property and is coated with a cross-linkable adhesive. The cooperative touch fasteners can be used to alter garments, hang window coverings and attach finishing covers. Additionally, the fasteners can be used in place of snaps and buttons, in medical devices, with diapers and in conjunction with a variety of manufacturing techniques.

29 Claims, 9 Drawing Sheets

U.S. PATENT DOCUMENTS

| | | |
|---|---|---|
| 5,786,062 A | 7/1998 | Callahan, Jr. et al. |
| 5,804,011 A | 9/1998 | Dutta et al. |
| 5,900,350 A | 5/1999 | Provost et al. |
| 5,945,131 A | 8/1999 | Harvey et al. |
| 5,996,189 A | 12/1999 | Wang |
| 6,136,944 A | 10/2000 | Stewart et al. |
| 6,185,745 B1 | 2/2001 | Alger |
| 6,205,623 B1 | 3/2001 | Shepard et al. |
| 6,241,567 B1 | 6/2001 | Evans |
| 6,248,450 B1 | 6/2001 | Voss et al. |
| 6,339,866 B1 | 1/2002 | French |
| 6,397,393 B1 | 6/2002 | Alger |
| 6,406,577 B1 | 6/2002 | Benedict et al. |
| 6,484,371 B1 * | 11/2002 | Romanko et al. ............. 24/306 |
| 6,579,915 B1 * | 6/2003 | Kroll et al. ................. 522/109 |
| 2001/0001300 A1 | 5/2001 | Tolbert et al. |
| 2002/0042455 A1 | 4/2002 | Simon et al. |

FOREIGN PATENT DOCUMENTS

| | | | |
|---|---|---|---|
| GB | 1 102 244 | | 2/1968 |
| JP | 2002-223818 | * | 8/2002 |
| WO | WO98/38262 | | 9/1998 |

OTHER PUBLICATIONS

Chris LeConte et al., Optimiazation of UV Curing Process for Adhesive Bonding in Medical Device Assembly, Application Note 089, pp. 1-4 (2002).

Velcro Brand Fastening Systems, "Product Information Guide," Provost Exhibit 2036B, pp. 1-5.

* cited by examiner

FASTENER TAPES

TECHNICAL FIELD

This invention relates to cooperative touch fasteners.

BACKGROUND

The majority of consumers purchase clothing and other garments in standard sizes, such as small, medium and large. Often times, these garments are not a perfect fit for the consumer. For example, if a person buys a shirt or coat that is large enough around the torso, the sleeves of the shirt might require shortening. The consumer can pay to have the garment altered, which for many is cost prohibitive, or if the consumer has the sewing skills and equipment, he can alter the garment himself. Frequently, the consumer has neither the money nor the skills to alter his clothing but instead wears clothes that don't have an ideal fit. Thus, it is desirable to provide to consumers a product that allows the user to alter clothing without sewing. It is also desirable that manufacturers be able to adjust the positioning of fasteners on products.

Improved means for adjusting and securing fasteners, particularly touch fasteners such as hook-and-loop or inter-engaging projection array fasteners, to underlying substrates are sought. Also sought are improved means of temporarily holding a fastener in place until permanent binding is achieved.

Some products employed to alter garments include a fabric tape which may be ironed on to a garment by melting a fusible resin, e.g., a thermoplastic polymer, carried on one surface of the tape (see, e.g., U.S. Pat. No. 5,006,393). Some tapes include cooperating touch fastener elements extending from the opposite surface of the tape. When the garment is subjected to heat greater than the melting point of the resin, as may occur during drying in a clothes dryer, the resin can melt and cause the tape to disengage from the garment.

SUMMARY

In general, the invention features positionable and securable cooperative touch fasteners and methods of making and using such touch fasteners. The touch fasteners can include a first surface carrying a plurality of fastener elements, and an opposite surface that carries a pressure sensitive adhesive that adheres the opposite surface to a substrate (e.g., fabric, leather, or wood) when pressure is applied to the touch fastener.

In one aspect, the invention features a touch fastener. The touch fastener includes a sheet-form base having an upper face and a lower face. A plurality of discrete fastener elements extend outwardly from the upper face of the base, and the lower face of the base includes an adhesive layer having a pressure-sensitive portion and a cross-linkable adhesive.

In some embodiments, the cross-linkable adhesive is also pressure sensitive, or is encapsulated in a pressure-sensitive adhesive in the pressure-sensitive portion.

In other embodiments, the lower face of the touch fastener has a first area of pressure sensitive adhesive and a second area of cross-linkable adhesive.

In some embodiments, the fastener elements are hooks. In some instances, the hooks are integrally molded with the upper face of the base. The hooks can have a height of less than about 0.05 inch (1.27 millimeters), e.g., between about 0.005 and 0.05 inch (0.127 and 1.27 millimeters). In some cases, the hooks are arranged in an array that covers substantially the entire upper face of the base. The hook density can be at least about 100 hooks per square inch (15.5 hooks per square centimeter), e.g., at least about 1000 hooks per square inch (155 hooks per square centimeter). In some cases, the fastener elements include stems with rounded or planar heads (i.e., mushrooms). In some cases, the fastener elements include palm tree hooks.

In some embodiments, the fastener elements are loops. The loops can be of a knit, woven, or non-woven material.

In some cases, the base is a woven material from which the fastener elements extend as filament ends.

In some embodiments, the cross-linkable adhesive is heat activated, e.g., a curable hot melt adhesive or a urethane.

In other embodiments, the cross-linkable adhesive is moisture activated, e.g., a urathane.

In some embodiments the cross-linkable adhesive is radiation activated, e.g., acrylic. The radiation can be UV, for example.

In some embodiments, the touch fastener further comprises a release liner covering the pressure-sensitive portion.

In another aspect, the invention features a method of permanently bonding a touch fastener to a material. The method includes providing a touch fastener having a sheet-form base with an upper face and a lower face. A plurality of discrete fastener elements extend outwardly from the upper face of the base, and the lower face includes an adhesive layer with a pressure-sensitive portion and a cross-linkable adhesive. The touch fastener is pressed against the material to temporarily adhere the touch fastener to the material in a desired location. Then the touch fastener is permanently bonded to the material by cross-linking the cross-linkable adhesive in the desired location.

In another aspect, the invention features a method of positioning a touch fastener. The method includes adhering a touch fastener with pressure at an initial location on a material. The touch fastener has a sheet-form base with an upper face and a lower face. A plurality of discrete fastener elements extend outwardly from the upper face of the base, and the lower face has an adhesive layer with a pressure-sensitive portion and a cross-linkable adhesive. Thereafter, the method includes determining whether the initial location of the touch fastener is a desirable location, if the initial location is not a desirable location, the touch fastener is repositioned to a second location. Once the touch fastener is in a desirable location, the cross-linkable adhesive is cross-linked, thereby permanently bonding the touch fastener to the desirable location on the material.

Another aspect of the invention features a method of altering a garment. The method includes temporarily adhering a first portion of a touch fastener to one region of a garment, the first portion of the touch fastener having a sheet-form base with an upper face and a lower face. A plurality of discrete fastener elements extend outwardly from the upper face, and the lower face has an adhesive layer with a pressure-sensitive portion and a cross-linkable adhesive. The method further includes temporarily adhering a second portion of a touch fastener to another region of the garment, the second portion of the touch fastener having a sheet-form base with an upper face and a lower face. A plurality of discrete fastener elements extend outwardly from the upper face of the base of the second portion and are configured to engage the fastener elements of the first portion, and the lower face has an adhesive layer with a pressure-sensitive portion and a cross-linkable adhesive. It is determined whether the first and second portions are at desirable initial locations and if necessary either or both of the first and second portions are repositioned. Once each of the first and second touch fastener portions is in a desirable location, it is permanently bonded to a respective region of the fabric by cross-linking the cross-linkable adhesive. The touch fasteners are then fastened by touching the first and second portions together, thereby altering the garment.

In some embodiments, the alteration includes changing the hem of a pant or changing the length of a sleeve.

In another aspect, the invention features a method of hanging window coverings. The method includes temporarily adhering on one region of a window covering a first portion of a touch fastener having a sheet-form base with an upper face and a lower face. A plurality of discrete fastener elements extend outwardly from the upper face, and the lower face has an adhesive layer with a pressure-sensitive portion and a cross-linkable adhesive. The method further includes temporarily adhering at an initial location on a wooden piece adjacent to a window a second portion of a touch fastener having a sheet-form base with an upper face and a lower face. A plurality of discrete fastener elements extend outwardly from the upper face of the base of the second portion and are configured to engage the fastener elements of the first portion, and the lower face has an adhesive layer with a pressure-sensitive portion and a cross-linkable adhesive. It is determined whether the first and second portions are at desirable initial locations and if necessary, either or both of the first and second portions are repositioned. Once each of the first and second touch fastener portions is in a desirable location, it is permanently bonded to the respective region of the wooden piece adjacent to the window or the window covering by cross-linking the cross-linkable adhesive. The touch fasteners are then fastened together by touching the first and second portions together, thereby hanging the window covering.

In another aspect, the invention features method of covering a furnishing with a material. The method includes temporarily adhering a first portion of a touch fastener to a region of a material, the first portion of the touch fastener having a sheet-form base with an upper face and a lower face. A plurality of discrete fastener elements extend outwardly from the upper face, and the lower face has an adhesive layer with a pressure-sensitive portion and a cross-linkable adhesive. The method further includes temporarily adhering a second portion of a touch fastener to one region of the furnishing, the second portion of a touch fastener having a sheet-form base with an upper face and a lower face. A plurality of discrete fastener elements extend outwardly from the upper face of the base of the second portion and are configured to engage the fastener elements of the first portion, and the lower face has an adhesive layer with a pressure-sensitive portion and a cross-linkable adhesive. It is determined whether the first and second portions are at desirable initial locations, and if necessary either or both of the first and second portions are repositioned. Once each of the first and second touch fastener portions is in a desirable location, it is permanently bonded to a respective region of either the material or the furnishing by cross-linking the cross-linkable adhesive. The touch fasteners are then fastened together by touching the first and second portions together, thereby covering the furnishing with material.

In some embodiments the furnishing is a chair, a table or a sofa.

In another aspect, the invention is a method of attaching bedding to a sleeping apparatus. The method includes temporarily adhering a first portion of a touch fastener to one region of a bedding article, the touch fastener having a sheet-form base with an upper face and a lower face. A plurality of discrete fastener elements extend outwardly from the upper face, and the lower face has an adhesive layer with a pressure-sensitive portion and a cross-linkable adhesive. The method further includes temporarily adhering a second portion of a touch fastener to one region of a sleeping apparatus, the second portion of the touch fastener having a sheet-form base with an upper face and a lower face. A plurality of discrete fastener elements extend outwardly from the upper face of the base of the second portion and are configured to engage the fastener elements of the first portion, and the lower face has an adhesive layer with a pressure-sensitive portion and a cross-linkable adhesive. It is determined whether the first and second portions are at desirable initial locations on either the bedding article or sleeping apparatus, and repositioning either or both of the first and second portions as necessary. Once each of the first and second touch fastener portions is in a desirable location, it is permanently bonded to the respective region of the sleeping apparatus or the bedding article by cross-linking the cross-linkable adhesive. The touch fasteners are then fastened together by touching the first and second portions together, thereby attaching the bedding to the sleeping apparatus.

In some embodiments the bedding article is a sheet. In other embodiments, the bedding article is a bed skirt.

In some embodiments, the sleeping apparatus is a bed.

In another aspect, the invention features a method of providing a closing means in an article. The method includes temporarily adhering a first portion of a touch fastener to one region of an article, the first portion of the touch fastener having a sheet-form base with an upper face and a lower face. A plurality of discrete fastener elements extend outwardly from the upper face of the base, and the lower face has an adhesive layer with a pressure-sensitive portion and a cross-linkable adhesive. The method further comprises temporarily adhering a second portion of a touch fastener to another region of the article, the second portion of the touch fastener having a sheet-form base with an upper face and a lower face. A plurality of discrete fastener elements extend outwardly from the upper face of the base of the second portion and are configured to engage the fastener elements of the first portion, and the lower face has an adhesive layer with a pressure-sensitive portion and a cross-linkable adhesive. It is determined whether the first and second portions are at desirable initial locations on the article, and either or both of the first and second portions are repositioned as necessary. Once each of the first and second touch fastener portions is in a desirable location, it is permanently bonded to a respective region of the article by cross-linking the cross-linkable adhesive. The touch fasteners are then fastened together by touching the first and second portions together, thereby providing a closing means in the article.

In some embodiments, the article is a purse. In some cases, the purse is made of fabric. In other cases, the purse is made of leather. In still other embodiments, the purse is made from a combination of fabric and leather.

In some embodiments, the article is a sleeping bag.

In other embodiments, the article is a diaper or a medical device such as a knee, ankle, or wrist brace.

The application of pressure alone need not result in a permanent bond of the touch fastener to the material; rather, the touch fastener can be repositioned in the event that the initial position of the touch fastener on the substrate is not the desired position. Once the touch fastener is in the desired position, the user can cure a cross-linkable adhesive that can also be carried on the opposite surface of the touch fastener to provide a permanent chemical bond between the touch fastener and the substrate.

The pressure sensitive adhesive can provide a means of attaching the touch fastener to a material in a non-permanent manner. This can allow the user to reposition the touch fastener in the event that its initial position is not ideal. For example, if the touch fastener is being used to alter a garment, e.g., shorten a hem on a pant leg, the user might have to estimate the desired position of the touch fasteners. Because the touch fasteners can be repositionable, the user can alter the position of the touch fasteners in the event the initial position was not the most desired position, e.g., the length of the pants with the alteration is too long or too short.

In many applications, the touch fasteners will be exposed to heat and water, such as a washer and dryer. Adhesives that are heat-softenable (e.g., thermoplastics) are often unable to withstand laundering, in particular the heat from a dryer, and thus touch fasteners using such adhesives may fall off when subjected to such conditions. On the other hand, the cross-linkable polymer can provide a permanent bond between the touch fastener and the material that withstands heat as well as moisture.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
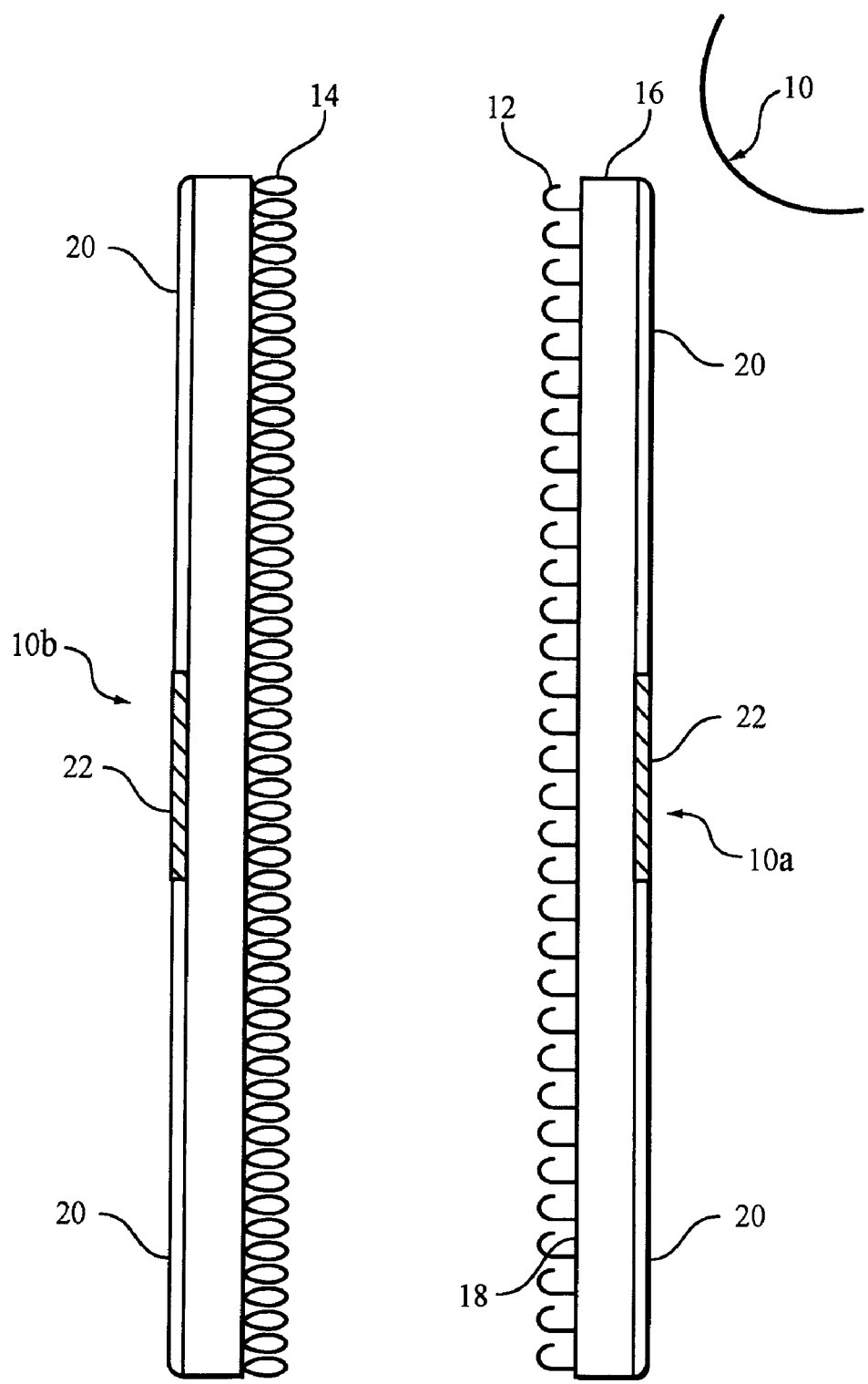
FIG. 1 depicts a side view of complementary touch fasteners, including the fastener elements, the sheet-form base, and adhesive.

Referring to FIG. 1, a touch fastener 10 includes a male fastener component 10a, and a female fastener component 10b. Each of the fastener components includes a plurality of cooperative touch fastener elements, i.e., hooks 12 on fastener component 10a, and loops 14 on fastener component 10b. The cooperative touch fastener elements extend from one surface 18 of a sheet-form base 16. The opposite surface of the base 16 is coated with a curable, cross-linkable adhesive 20, and a pressure sensitive adhesive 22.

The cooperative touch fasteners can be molded or woven. U.S. Pat. No. 5,945,131 is incorporated by reference in its entirety, and relates to molded touch fasteners having a plurality of discrete fastener elements that extend outwardly from, and integral with base layer, wherein stems of the fastener elements are integrally molded to the base. U.S. Pat. No. 5,996,189 is incorporated herein by reference in its entirety, and relates to woven touch fasteners having a main fabric body with a woven base and an array of fibrous fastener elements anchored to and projecting from the woven base.

Figure 2:
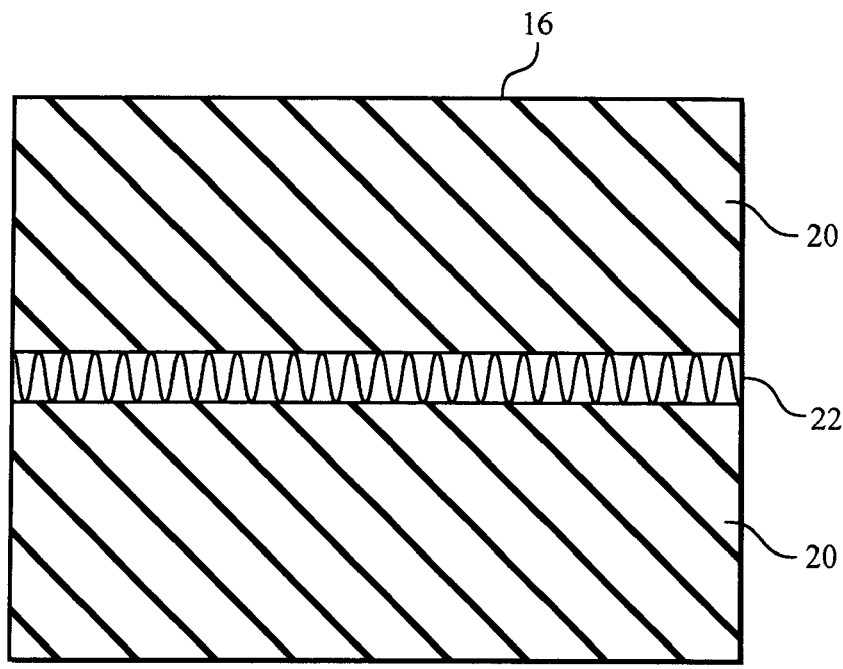
FIG. 2 depicts a view of the lower portion of the sheet-form base, wherein the sheet-form base is coated with a pressure sensitive adhesive and a cross-linkable adhesive.

As shown on FIG. 2, the bottom surface of the sheet-form base 16 includes distinct portions, a first portion being coated with the cross-linkable adhesive 20 and a second portion being coated with the pressure sensitive adhesive 22. In the embodiment shown in FIG. 2, the pressure sensitive adhesive 22 is coated as a strip in the middle portion of the sheet-form base 16, and the cross-linkable adhesive 20 is coated adjacent to the pressure sensitive adhesive on the either side of the strip of pressure sensitive adhesive.

Figure 4:
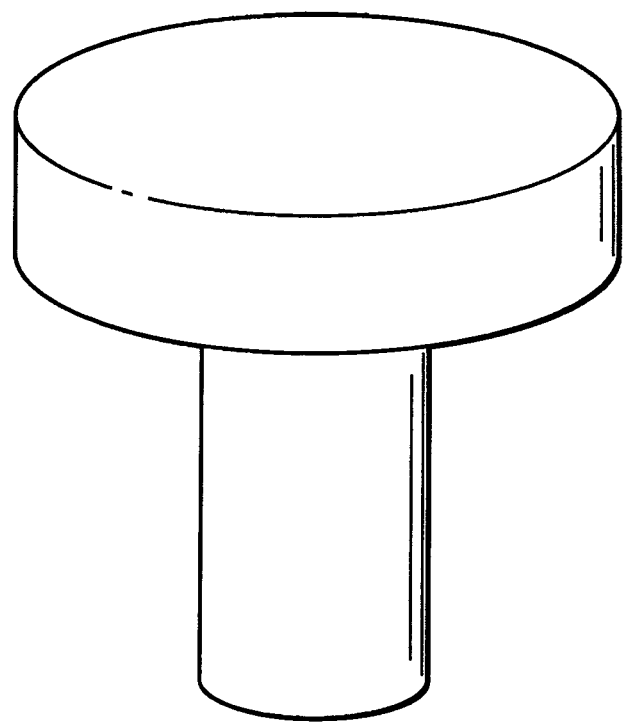
FIG. 4 is an enlarged perspective view of a flat-topped mushroom hook, used in an alternative embodiment of the invention.
Figure 5:
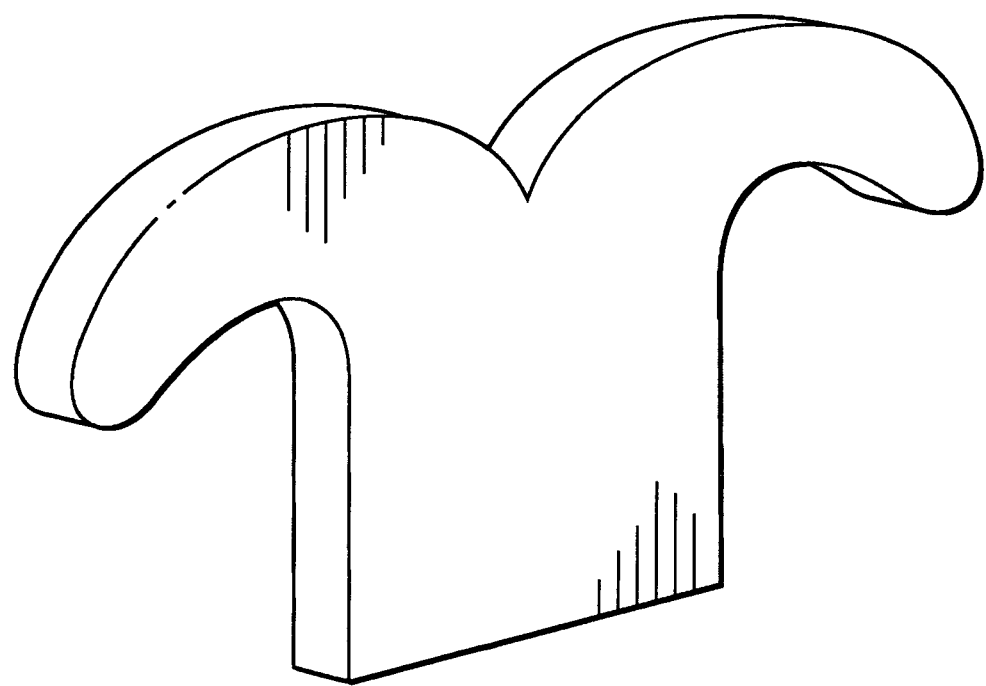
FIG. 5 is an enlarged perspective view of a palm tree hook, used in an alternative embodiment of the invention.

While the hooks shown in FIG. 1 are inverted J-shape hooks, other types of hooks can also be used. The hooks can be in many different shapes, including inverted J-shape, flat-topped mushroom (FIG. 4), and palm tree (FIG. 5). The loops shown in FIG. 1 can be any structure or material known in the art, for example, the loop can be of a knit, woven, or non-woven material, and can be of filaments or fibers comprising nylons, polyesters, polypropylenes, or co-polymers thereof, as examples.

The pressure sensitive adhesive 22 provides a means of attaching the touch fastener to a material (such as fabric, wood, or leather) in a non-permanent manner. This non-permanent attachment allows the user to attach the touch fastener to a garment or other item, determine whether the touch fastener is in the ideal position, and then reposition the touch fastener in the event that the initial position is not in the ideal position. Examples of pressure sensitive adhesives include water-based adhesives such as those commercially available from National Starch Nacor® (72-8685) or Bostik-Findley (M2289); and hot melt pressure sensitive adhesives such as those commercially available from Bostik-Findley (HL 2211).

In some instances, the pressure sensitive adhesive is water soluble, providing the benefit that once the adhesive is in place and cured, the pressure sensitive adhesive can be washed away, leaving only the permanent chemical bond of the cross-linked polymer.

Once the touch fastener is in the desired position, the user can permanently attach the touch fastener to the material by curing the cross-linkable adhesive 20. The cross-linkable adhesives are generally polymers. The curing (i.e., cross-linking) of the polymer generally requires an initiating event and can be accomplished by a variety of means that are generally dependent on the polymer. Some means of initiating cross-linking of polymers include heat (e.g., iron, blow dryer, hot air gun, or heated nip roll), moisture (e.g., water or steam), and radiation (e.g., infrared, RF, uv or microwave).

Examples of moisture cure adhesives include curable hot melt adhesives and urethanes. Such adhesives are commercially available, e.g., from Bostik-Findley, Adhesive Films, and Gorilla Glue®.

Examples of heat-cured adhesives include curable hot melt adhesives and urethane. Such adhesives are commercially available, e.g., from Bostik-Findley, Adhesive Films, Adhesives Research Inc and Bemis.

Examples of radiation-cured adhesives include acrylic, epoxies, silicones, acrylates, olefins, and urethanes. Where a radiation cured polymer is used, the sheet form base can be fashioned to have some degree of transparency, thus allowing radiation applied at the front face of the fastener to reach the polymer and effect the cross-linking. Alternatively, the sheet form base can include holes, allowing the radiation to reach areas of the cross-linking adhesive, to provide a permanent bond of the touch fastener to the material.

The cross-linkable adhesive, once cured, forms a permanent chemical bond between the sheet-form base and the material. The resulting chemical bond is resistant to conditions such as moisture and heat and therefore is useful in applications where the desired product is exposed to water (e.g., a washing machine or rain) and/or heat (e.g., a drying machine or summer sun).

The adhesive may be applied to the lower face of the sheet-form base using any desired coating or laminating technique, e.g., by laminating a transfer film to the base with a heated nip roll.

In some embodiments, the touch fasteners are used as a tool for the alteration of garments (e.g., hemming pants, shortening sleeves, altering the length of a jacket). The touch fasteners provide a practical means of fitting a garment for persons without the time, skills or the required equipment needed to provide alterations by sewing the garment. While clothing is sold in standard sizes for the person of a set proportion, not all consumers fit the proportions of clothing sold on the rack. However, the alteration of clothing can be expensive, and for many consumers is cost prohibitive.

Figure 6A:
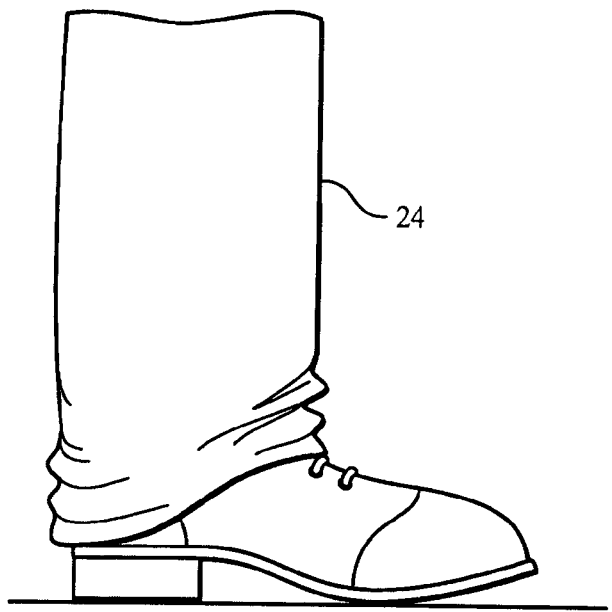
FIGS. 6a–6c depict a schematic representation of the use of touch fasteners to alter the length of a pant leg.
Figure 6C:
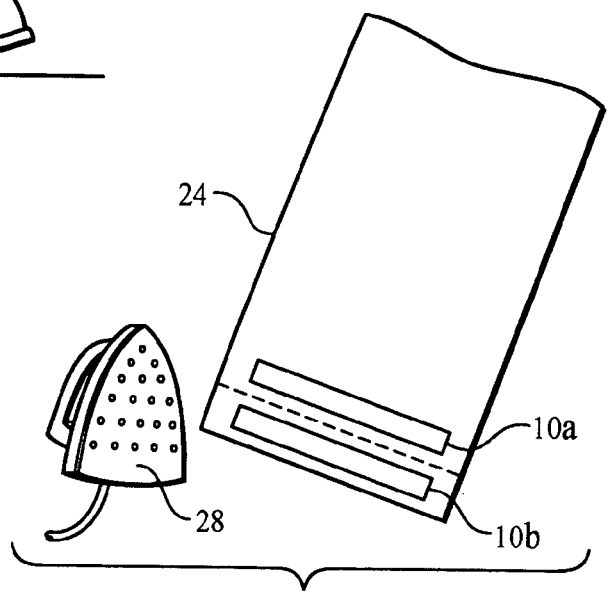
Figure 6B:
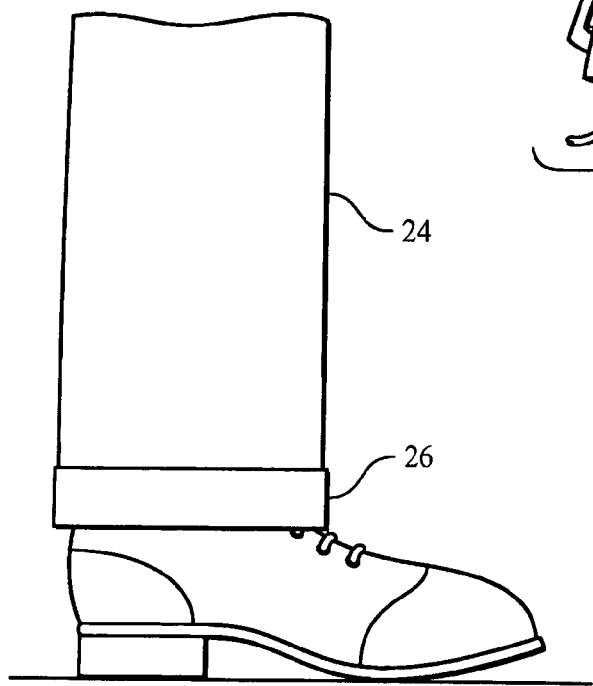

FIGS. 6a–6c provide a schematic diagram of a consumer altering a garment using the cooperative touch fasteners 10a and 10b shown in FIG. 1. Referring to FIG. 6a, a user has purchased a pair of pants 24 that need to be altered (i.e., shortened). The user can initially try on the pants 24, folding the leg of the pant in the desired position, e.g., to have a cuff 26 as shown in FIG. 6b. As shown in FIG. 6c, after trying on the pants 24, the user can remove the pants and position the cooperative touch fasteners 10a and 10b so that the female touch fastener and male touch fastener, when contacting each other, produce the desired pant length, i.e., by providing cuff 26. In some instances, the user is trying on the pants 24 without the aid of another person, and therefore must estimate the location of the fold and location of the touch fasteners 10a and 10b. Because the touch fasteners are repositionable, the user can try on and reposition the touch fasteners repeatedly until the desired length is achieved. For example, the user can position the female touch fastener 10b, and reposition only the male fastener 10a, to adjust the size of the fold and thus the length of the pants. Once both the female and male touch fasteners are in the desired position, the user can permanently attach them to the garment, for example by using heat and/or steam from an iron 28 (see FIG. 6c). Thus, the touch fasteners allow the length of the pants to be easily altered without the need for a tailor or sewing skills or equipment.

Figure 7A:
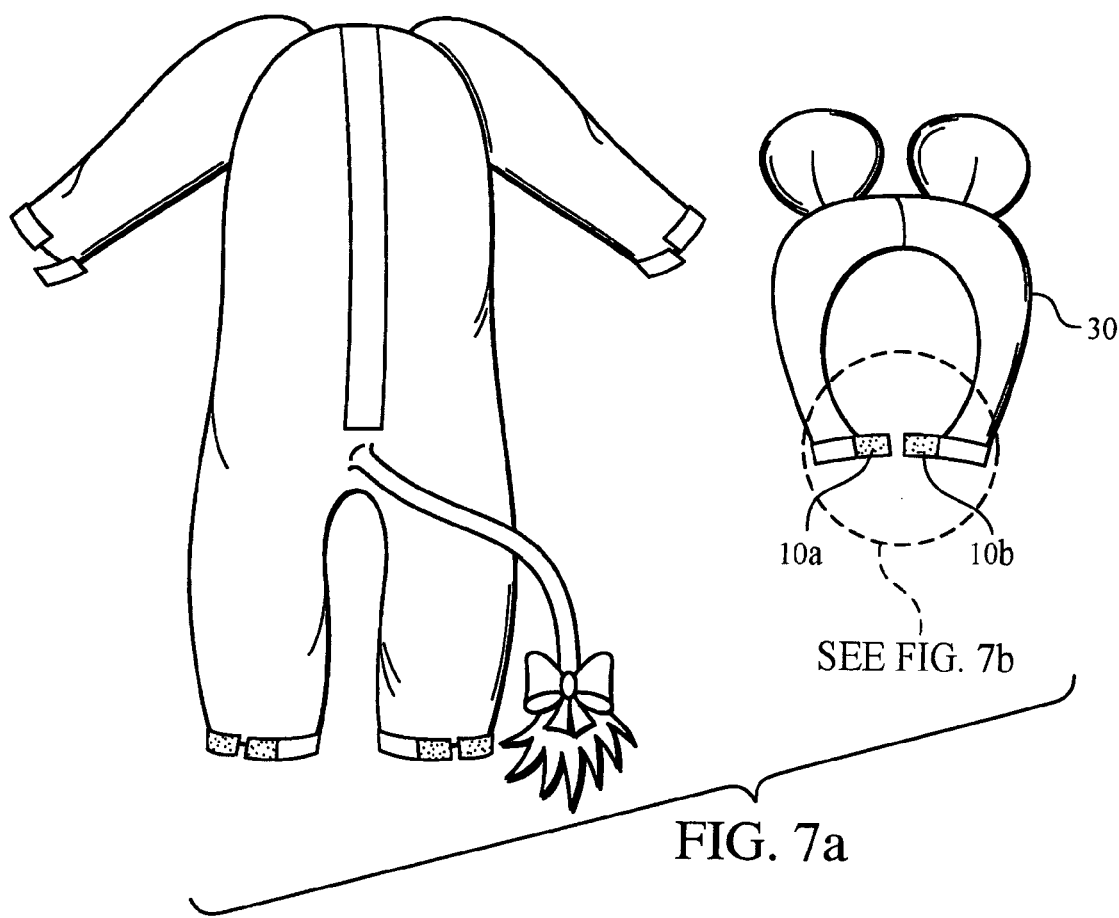
FIGS. 7a–7b depict a diagrammatic representation of the use of touch fasteners as an alternative to buttons or snaps.
Figure 7B:
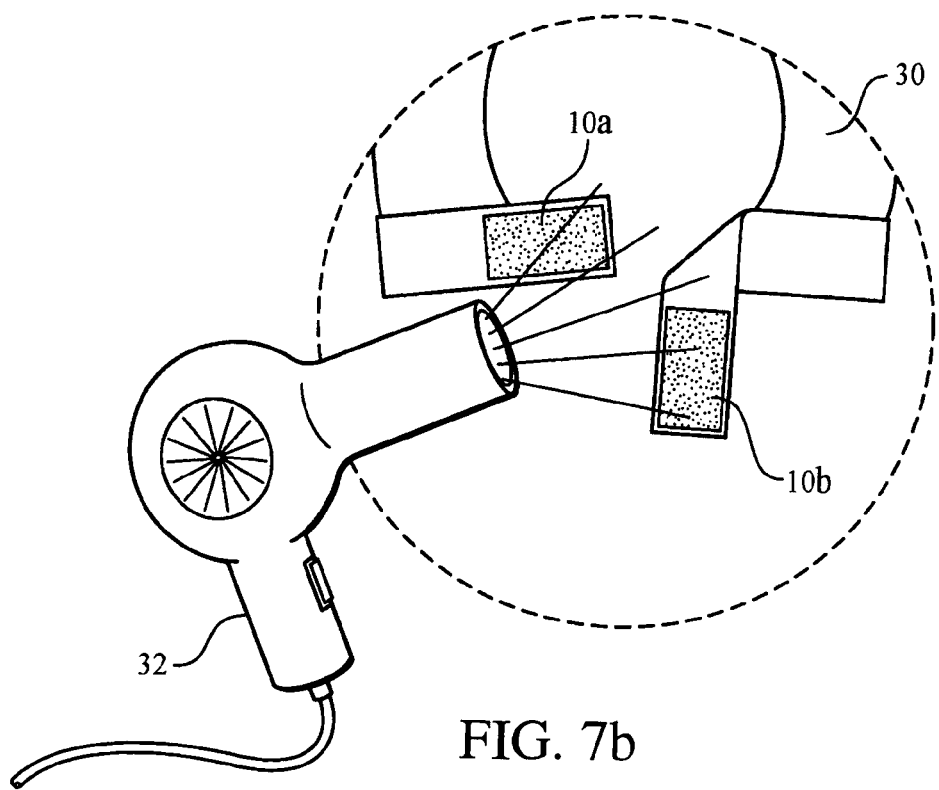

The cooperative touch fasteners can also be used as a replacement for snaps and buttons. For example, referring to FIG. 7a, the cooperative touch fasteners 10a and 10b are positioned on a headpiece 30. To place the garment in position, i.e., to cover the head of the user with the headpiece 30, the opening on the headpiece 30, must be relatively large. However, once the headpiece 30 is in position, the opening needs to be closed to provide a snug fit for the user. Whereas the use of buttons or snaps requires sewing, the same function can be achieved using the cooperative touch fasteners, which can be attached without any sewing at all. Additionally, the male and female touch fasteners 10a and 10b are repositionable, allowing the headpiece 30 to be adjusted until the touch fasteners are in the ideal position to precisely fit the user. Referring to FIG. 7b, once in the desired location on the headpiece 30, the touch fasteners 10a and 10b can be permanently attached using the heat from a hair dryer 32 to cure the cross-linkable adhesive.

Figure 8A:
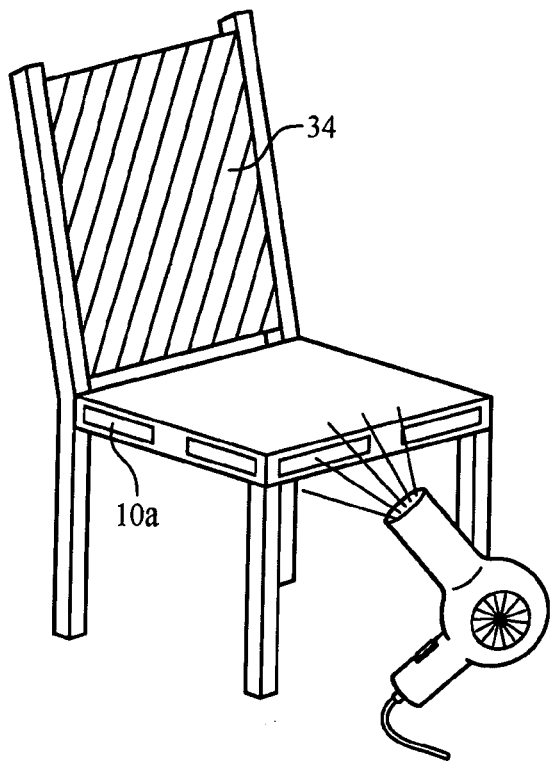
FIGS. 8a–8d depict a schematic representation of the use of touch fasteners to cover a chair with material.

The touch fasteners can be used to attach a chair covering material to a chair. Referring to FIG. 8a, male touch fasteners 10a are positioned on the chair 34 (e.g., on a wooden portion of the chair), and, once positioned in the proper location, are permanently bonded to the chair using heat from a hair dryer 32. The cooperative touch fasteners 10b are positioned on the chair covering material 36.

Figure 8B:
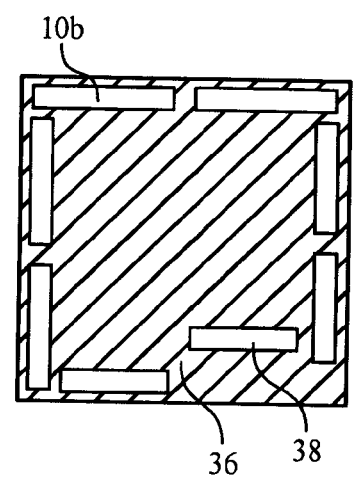
Figure 8D:
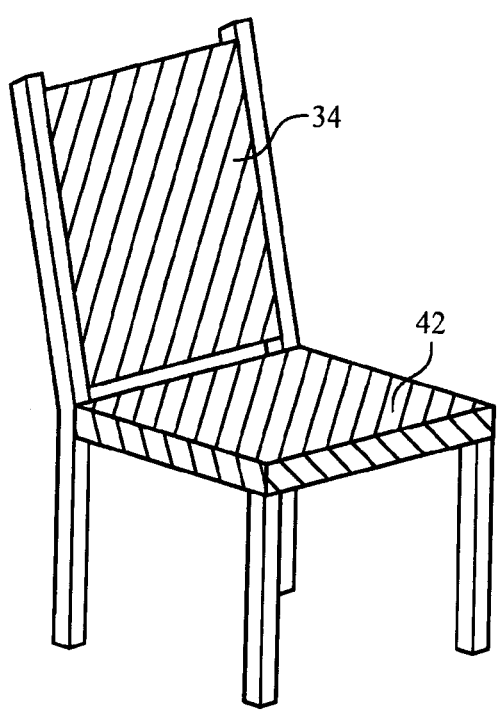
Figure 8C:
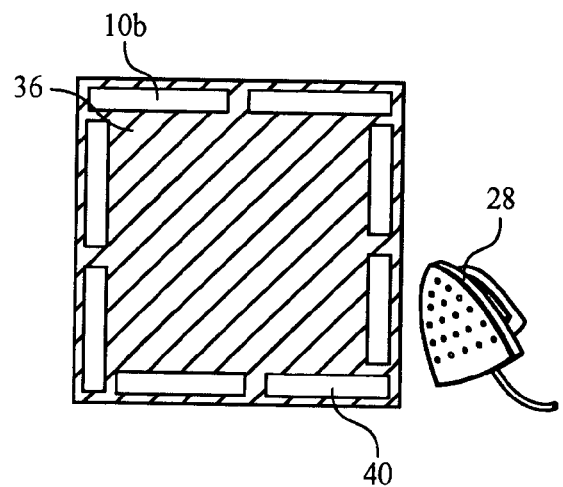

Referring to FIGS. 8b and 8c, if touch fastener 10b is positioned incorrectly when initially positioned on the material 36, the touch fastener 10b can be removed from its initial position 38 on the material 36, and repositioned to a preferred position 40 by reapplying pressure to the touch fastener. Once the touch fastener 10b is in the desired location, it is then permanently attached by curing the cross-linkable adhesive, e.g., using the heat from an iron 28.

The chair 34 is then covered by contacting the touch fasteners together (see FIG. 8d). While the cooperative touch fasteners are permanently attached to the material 36, and chair 34, respectively, the touch fasteners are not permanently attached to each other, but rather the user can disengage the touch fasteners to remove the material 36 from the chair 34. This allows the user to change the chair covers without damage to the material 36 or to the chair 34. For example, using the touch fasteners, the user can change the material seasonally, or even more frequently depending on taste. Moreover, since removal of the chair covering material does not damage the material, the same chair covering can be reused at a later date. This decorating flexibility is not provided by traditional means of attachment (e.g. glue, staples, or stitching).

Figure 9A:
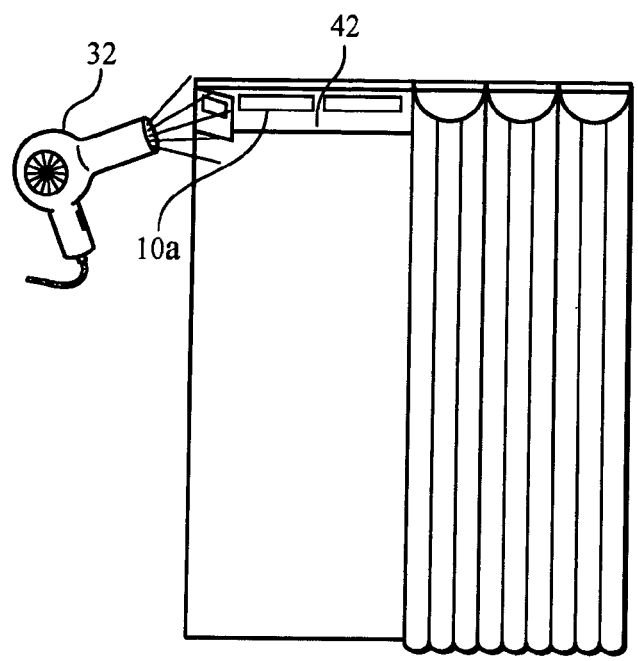
FIGS. 9a–9c depict a schematic representation of the use of touch fasteners to hang window coverings.
Figure 9B:
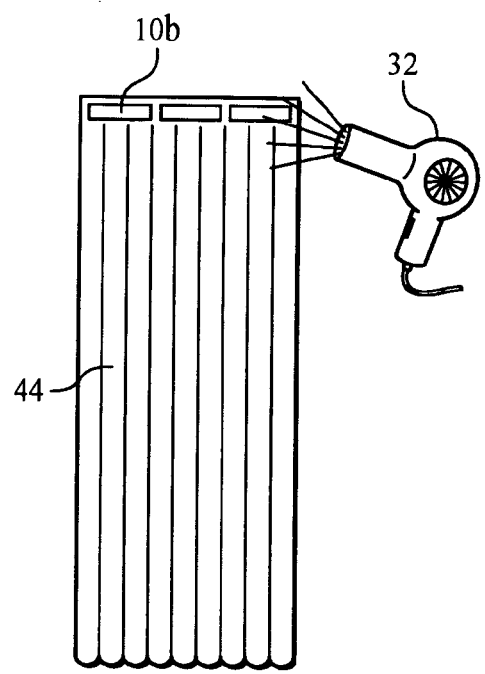
Figure 9C:
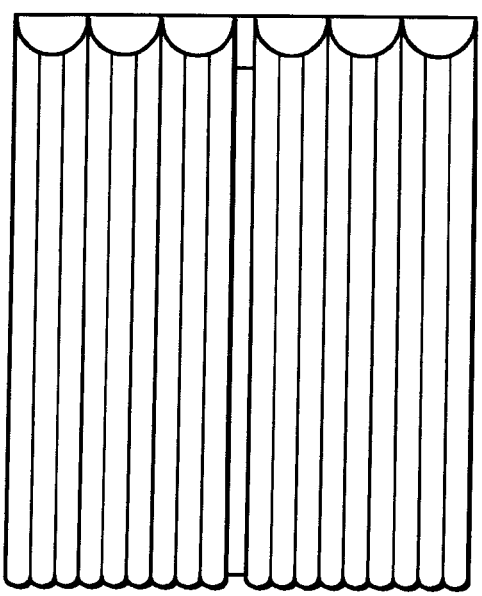

The touch fasteners can also be used to hang window coverings (e.g., curtains). Referring to FIGS. 9a and 9b, the male touch fasteners 10a are positioned on a wooden support or window frame adjacent a window 42 (e.g., at the top of the window), and the female touch fasteners 10b are attached to the curtain material 44, in the same manner discussed above with reference to FIGS. 8a–8d. Once correctly positioned on the window and on the material, the touch fasteners are permanently attached by curing the cross-linkable adhesive with heat from a hair dryer 32. The curtain material 44 is then hung by contacting the cooperative touch fasteners, 10a and 10b, together (see FIG. 9c), properly positioned for a visually pleasing appearance.

FIG. 10 shows an example of the use of touch fasteners to provide a closure for a purse 46 (e.g., a substitute for a zipper or a snap). While not all purses are sold having a closure, often such a closure is desirable to provide deterrence for pickpockets and to prevent items from falling out of the opening 48 of the purse 46. Using the cooperative touch fasteners, the consumer can add just such a feature to a purse. Male touch fastener components 10a are positioned on the top, inside edge of the rear portion of the purse 46.

Figure 10A:
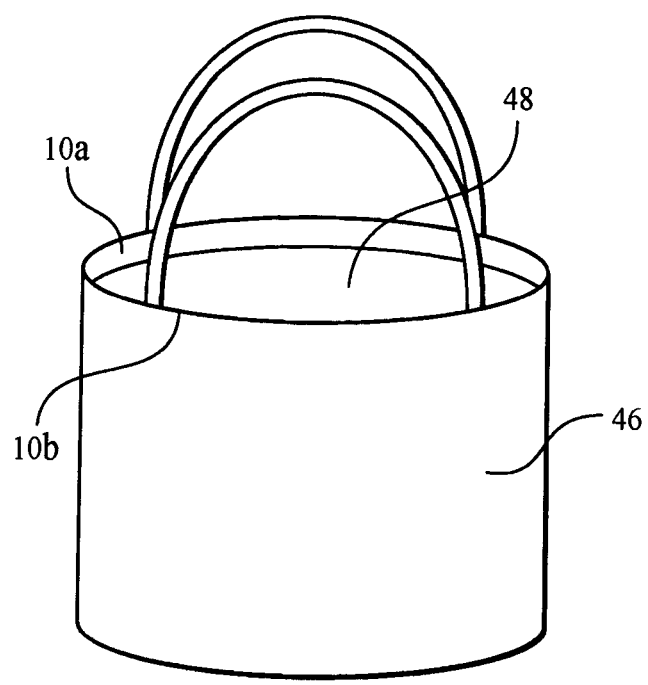
FIGS. 10a–10b depict a schematic representation of the use of touch fasteners to provide a closing mechanism in a purse.
Figure 10B:
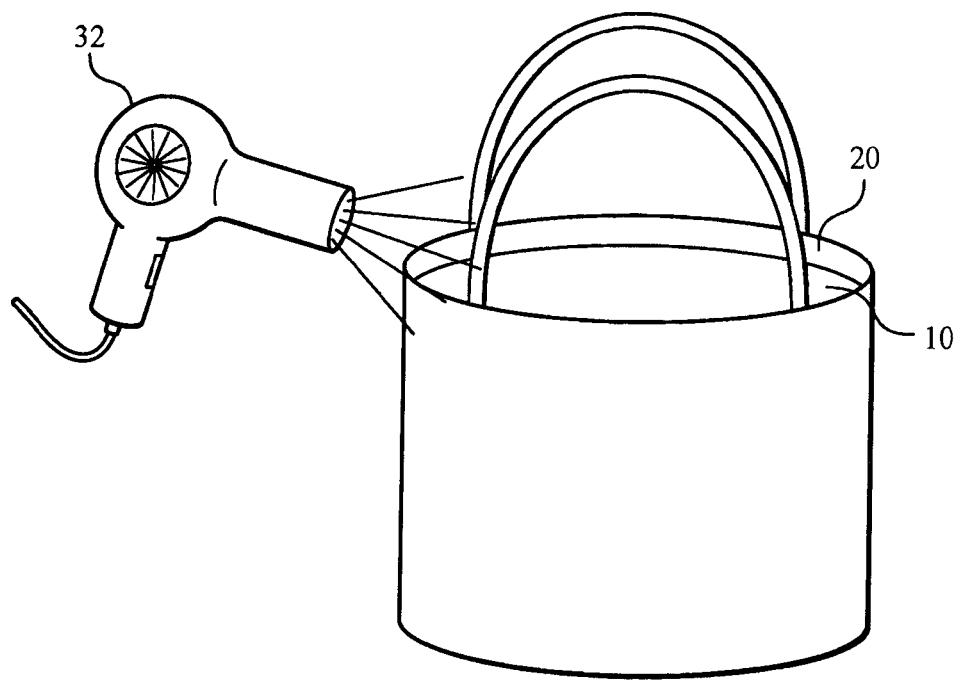

Female touch fastener components 10b are positioned on the top, inside edge of the front portion of the purse 46 (see FIG. 10a). Once the touch fasteners are correctly positioned, the cross-linkable adhesive is cured using heat from a blow dryer 32 (see FIG. 10b).

As described above, the touch fasteners can be permanently bonded to a fabric by cross-linking the cross-linkable adhesive. In many applications, this means of attachment is preferable to conventional means such as attaching the touch fastener by sewing it to the fabric, as the nature of sewing necessarily causes holes in the material. The presence of holes in a material is often undesirable where the touch fasteners are attached to a material used as a water resistant barrier. For example, the touch fasteners can be permanently bonded to a weather resistant jacket (e.g., a jacket made from Gore-Tex®), without causing holes or punctures in the fabrics as would be caused when sewing on a zipper, button or snaps. Other examples where the cross-linking means of attachment is preferable to more conventional means includes attaching a water resistant covering to a tent or to an object such as an umbrella to protect people or objects from the elements such as rain or snow.

Additionally, the cooperative touch fasteners 10a and 10b can be used to provide a means of temporarily attaching one garment to another. For example, to help prevent the loss of winter accessories such as scarves and gloves, the cooperative touch fasteners can be used to provide an attachment point to secure, for example, a scarf to the collar of a coat.

While the examples shown in FIGS. 7–10b utilize heat from a hair dryer as a curing means, any suitable curing means can be used. For example, heat or moisture curable polymers can be used, and the polymer can be cured with heat or steam from an iron.

The touch fasteners can also be used in the manufacture of items made by hand, or for prototyping. For example, if a small amount of an article is being produced and it is not economical to automate the production, the cooperative touch fasteners provide the ability to quickly manufacture an article for testing by allowing portions of the article to be positioned and repositioned as required for an accurate fit. For example, the touch fasteners can be used when positioning straps on a shirt or a purse. The cooperative touch fasteners 10a and 10b can be positioned, e.g., on the strap and on the body of the shirt. Once positioned, the user can try on the shirt, and reposition the straps and touch fasteners 10a and 10b as desired. Once the touch fasteners 10a and 10b are positioned such that the article is correctly fitted, the touch fasteners can be cross-linked to permanently attach them to the article.

In addition to clothing, the touch fasteners can be used to custom fit medical devices such as a wrist, ankle or knee brace. The person wearing the brace can try various positions for attachment and adjust the position of the touch fasteners 10a and 10b (or at least one of 10a and 10b) to provide an accurate fit (i.e., to prevent restricting circulation or prevent shifting of the brace, maintaining it in a desired position). Once in a desired position, the touch fasteners 10a and/or 10b can be cross-linked to become permanently attached to the medical device.

Figure 11A:
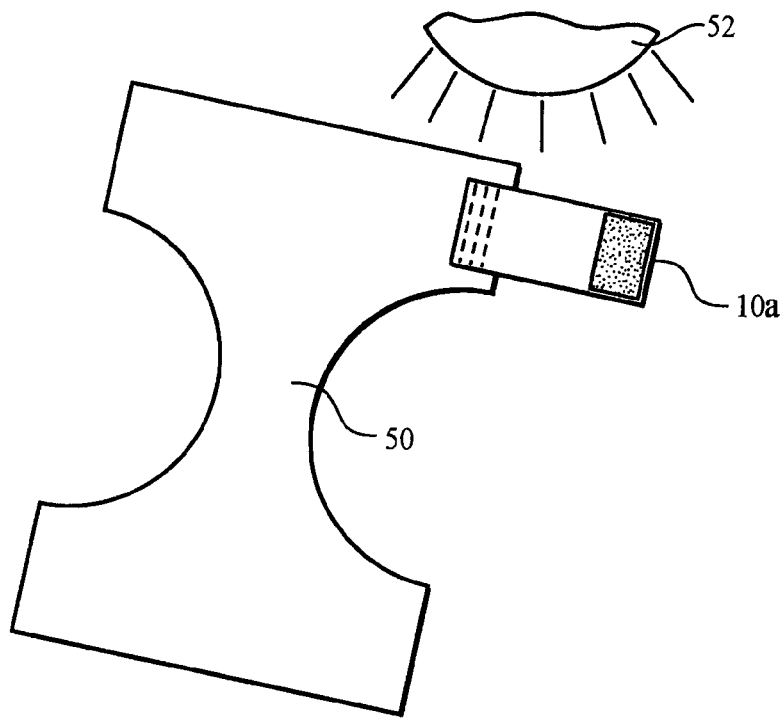
FIGS. 11a–11c depict a diagrammatic representation of the use of touch fasteners in the manufacture of diapers.
Figure 11B:
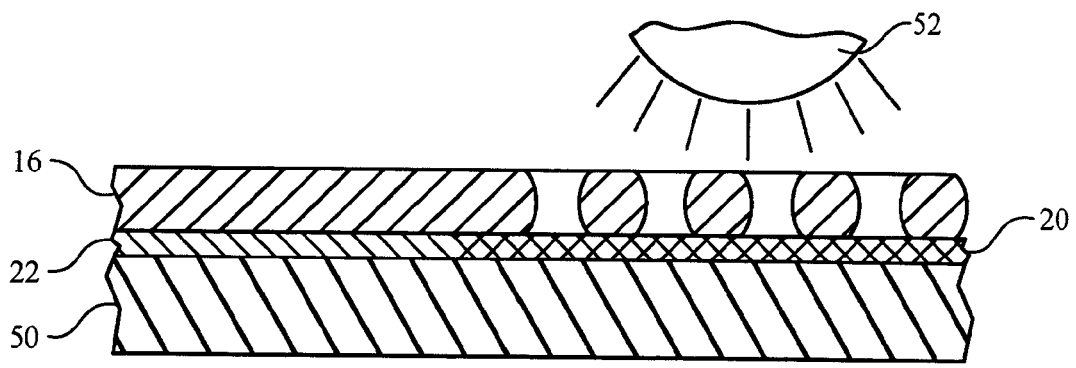
Figure 11C:
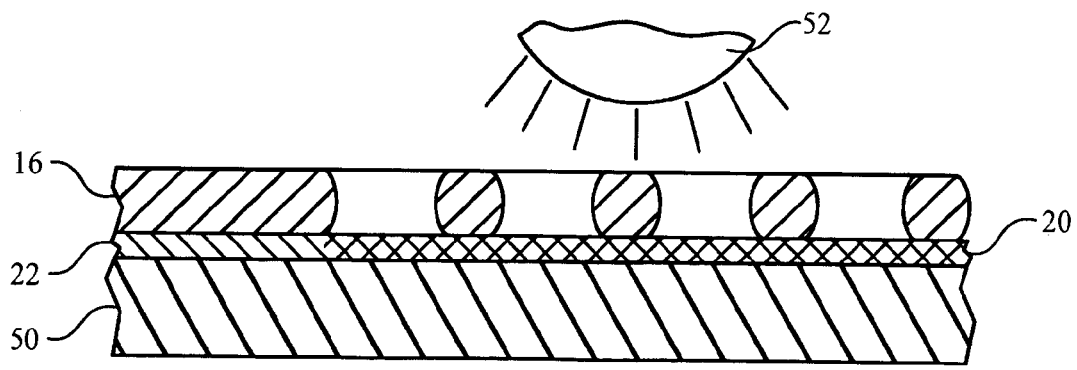

The touch fasteners 10a and 10b can be used as a means of attachment in diapers. For example, during manufacture, a touch fastener 10a can be stamped onto a diaper 50 to provide a temporary means of attachment. As shown in FIG. 11a, the touch fastener can then be permanently attached using a source of radiation 52, such as a UV lamp to then permanently bond the touch fastener to the diaper 50, without the need for additional contact with the diaper or touch fastener. Where radiation curable adhesives are used, the sheet form base 16 can be of a transparent material, allowing the radiation to reach the cross-linkable adhesive 22. Alternatively, the sheet form base 16 can include holes, allowing the radiation to reach portions of the cross-linkable adhesive, to secure a permanent connection of the touch fastener 10a to the material. As seen in FIGS. 11b and 11c, the holes in the sheet-form base can be of varying sizes.

The applications described above are examples of the wide variety of consumer and manufacturing applications in which the cooperative touch fasteners can be used. These cooperative touch fasteners also have other applications, for example with wall hangings. The desired size and shape of the cooperative touch fastener is dependent on the application of the user. For example, the length and width of the touch fasteners can vary with the intended use. In some instances, the touch fastener can be formed in the shape of a long strip, similar to that of tape, allowing the user to cut the touch fastener to the desired length. Alternatively, the touch fastener can be in the shape of circles, squares, or rectangles of various sizes, or can be in the form of a sheet, allowing the user to cut the touch fastener to a desired shape.

It is important to prevent the premature curing of the cross-linkable adhesive so that the cross-linkable adhesive will still be in a curable condition when the user wishes to permanently attach the touch fastener to a surface. For example, where the cross-linkable adhesive is moisture sensitive, the touch fastener can be stored in an air-tight package to prevent the adhesive from curing as a result of contact with ambient air and moisture. The user can then break the seal of the package prior to the use of the touch fastener.

The sheet-form base can be covered with a release liner to protect the pressure sensitive adhesive and prevent exposure of the adhesive to moisture. The user then removes the release liner from the sheet-form base just prior to use.

Figure 3:
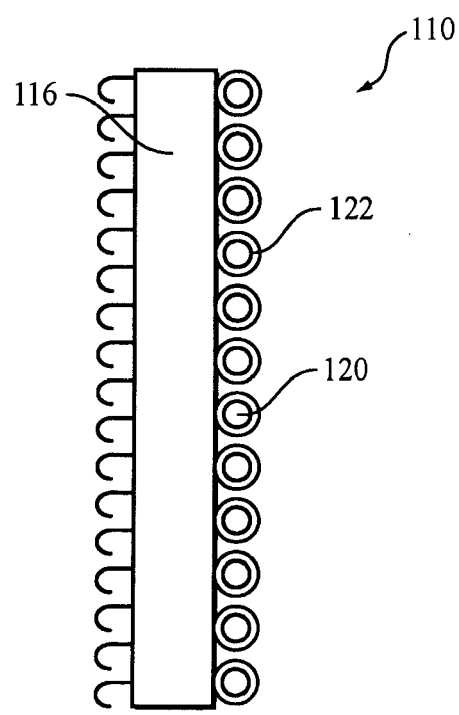
FIG. 3 depicts a view of the lower portion of the sheet-form base, wherein the sheet-form base is coated with a cross-linkable adhesive that is encapsulated in a pressure sensitive adhesive.

While FIG. 2 depicts one example of a sheet-form base coated with discrete portions of a pressure sensitive adhesive and a cross-linkable adhesive, FIG. 3 depicts another embodiment, in which a sheet-form base 116 is coated with a cross-linkable adhesive 120 that is encapsulated within a pressure sensitive adhesive 122. In this case, a user activates the adhesive using pressure. The pressure breaks the encapsulation, which exposes the cross-linkable adhesive 20 to the material, thus allowing the cross-linkable adhesive to chemically bond to the material upon curing.

In some embodiments, the adhesive is both pressure sensitive and cross-linkable, and thus the sheet-form base is coated with a single adhesive. In this instance, the adhesive is initially pressure sensitive and non-cross-linked. Application of both heat and pressure (e.g., application of an iron) cross-links the adhesive, thus permanently bonding the touch fasteners to the material.

In some embodiments, the adhesive is a semi-tacky, heat activated adhesive. The adhesive coating, as applied to the sheet-form base 16, has a light tacky quality, providing pressure sensitive adhesive properties. The application of heat and or pressure to the sheet-form base causes the adhesive to cross-link and thus permanently hold to the fabric. Such adhesives are commercially available, and can be purchased for example from Bostik-Findley, Adhesives Research Inc. and Collano. Some examples of such adhesives include Purbond® (HCM VN 55A, HCM VN5551) reactable urethane adhesives, which have adhesive peel values between 2 and 10 pounds per inch width.

In some embodiments, the sheet-form base is coated with a curable hot melt adhesive that is encapsulated into a pressure-sensitive hot melt adhesive. The adhesive is activated with pressure, as discussed above with reference to FIG. 3, exposing the curable hot melt adhesive. The curable hot melt adhesive may be, for example, a room temperature curable adhesive. Such adhesives are commercially available and can be purchased, e.g., from Spring Industries Inc.

A number of embodiments of the invention have been described. Nevertheless, it will be understood that various modifications may be made without departing from the spirit and scope of the invention. Accordingly, other embodiments are within the scope of the following claims.

What is claimed is:

1. A touch fastener comprising:
   a sheet-form base having an upper face and a lower face;
   extending outwardly from the upper face of the base, a plurality of discrete fastener elements; and
   the lower face including an adhesive layer having a pressure sensitive portion, and comprising a cross-linkable adhesive, wherein the pressure sensitive portion is pressure sensitive at room temperature and the cross-linkable adhesive is cross-linkable by a user to permanently secure the touch fastener to a substrate.

2. The touch fastener of claim 1, wherein the cross-linkable adhesive is also pressure sensitive.

3. The touch fastener of claim 1, wherein the cross-linkable adhesive is encapsulated in a pressure sensitive adhesive in the pressure-sensitive portion.

4. The touch fastener of claim 1, wherein the lower face comprises a first area of pressure sensitive adhesive and a second area of cross-linkable adhesive.

5. The touch fastener of claim 1, wherein the fastener elements comprise hooks.

6. The touch fastener of claim 5, wherein the hooks are integrally molded with the upper face of the base.

7. The touch fastener of claim 5, wherein the hooks have a height of less than about 0.05 inch (1.27 millimeters).

8. The touch fastener of claim 5, wherein the hooks have a height of between about 0.005 and 0.05 inch (0.127 and 1.27 millimeters).

9. The touch fastener of claim 5, wherein the hooks are arranged in an array uniformly covering substantially the entire upper face or the base.

10. The touch fastener of claim 5, wherein the hooks are arranged with a hook density of at least about 100 hooks per square inch (15.5 hooks per square centimeter).

11. The touch fastener of claim 10, wherein the hook density is at least about 1000 hooks per square inch (155 per square centimeter).

12. The touch fastener of claim 5, wherein the hooks are mushroom-shaped.

13. The touch fastener of claim 5, wherein the hooks comprise palm tree hooks.

14. The touch fastener of claim 1, wherein the fastener elements comprise loops.

15. The touch fastener of claim 14, wherein the loops are of a knit, woven, or non-woven material.

16. The touch fastener of claim 1, wherein the base is a woven material from which the fastener elements extend as filament ends.

17. The touch fastener of claim 1, wherein the cross-linkable adhesive is heat activated.

18. The touch fastener of claim 17, wherein the heat activated cross-linkable adhesive is a curable hot melt adhesive, or a urethane.

19. The touch fastener of claim 1, wherein the cross-linkable adhesive moisture activatable.

20. The touch fastener of claim 19, wherein the moisture activatable cross-linkable adhesive is a urethane.

21. The touch fastener of claim 1, wherein the cross-linkable adhesive is radiation activatable.

22. The touch fastener of claim 21, wherein the cross-linkable adhesive is UV activatable.

23. The touch fastener of claim 1, further comprising a release liner covering the pressure-sensitive portion.

24. A touch fastener comprising:
    a sheet-form base having an upper face and a lower face;
    extending outwardly from the upper face of the base, a plurality of discrete fastener elements; and
    the lower face including an adhesive layer have a pressure sensitive portion, and comprising a cross-linkable adhesive, wherein the cross-linkable adhesive is encapsulated in a pressure sensitive adhesive in the pressure-sensitive portion.

25. The touch fastener of claim 24, wherein the cross-linkable adhesive is heat activated.

26. The touch fastener of claim 25, wherein the heat activated cross-linkable adhesive is a curable hot melt adhesive, or a urethane.

27. A touch fastener comprising:
    a sheet-form base having an upper face and a lower face;
    extending outwardly from the upper face of the base, a plurality of discrete fastener elements; and
    the lower face including an adhesive layer have a pressure sensitive portion, and comprising a cross-linkable adhesive, wherein the lower face comprises a first area of pressure sensitive adhesive and a second area of cross-linkable adhesive.

28. The touch fastener of claim 27, wherein the cross-linkable adhesive is heat activated.

29. The touch fastener of claim 28, wherein the heat activated cross-linkable adhesive is a curable hot melt adhesive, or a urethane.

* * * * *